(12) United States Patent
Yamazaki et al.

(10) Patent No.: US 9,873,109 B2
(45) Date of Patent: Jan. 23, 2018

(54) CATALYSTS FOR THERMOCHEMICAL FUEL PRODUCTION AND METHOD OF PRODUCING FUEL USING THERMOCHEMICAL FUEL PRODUCTION

(71) Applicants: JAPAN SCIENCE AND TECHNOLOGY AGENCY, Saitama (JP); CALIFORNIA INSTITUTE OF TECHNOLOGY, Pasadena, CA (US)

(72) Inventors: Yoshihiro Yamazaki, Pasadena, CA (US); Sossina M. Haile, Pasadena, CA (US); Chih-Kai Yang, Pasadena, CA (US)

(73) Assignees: CALIFORNIA INSTITUTE OF TECHNOLOGY, Pasadena, CA (US); JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 14/595,130

(22) Filed: Jan. 12, 2015

(65) Prior Publication Data
US 2015/0125383 A1 May 7, 2015

Related U.S. Application Data

(62) Division of application No. 13/600,948, filed on Aug. 31, 2012, now abandoned.
(Continued)

(51) Int. Cl.
*B01J 23/889* (2006.01)
*B01J 23/34* (2006.01)
(Continued)

(52) U.S. Cl.
CPC ......... *B01J 23/8892* (2013.01); *B01J 23/002* (2013.01); *B01J 23/26* (2013.01);
(Continued)

(58) Field of Classification Search
CPC ........ B01J 23/8892; B01J 23/26; B01J 23/83; B01J 23/002; B01J 37/08; B01J 35/002;
(Continued)

(56) References Cited

U.S. PATENT DOCUMENTS

| 5,380,692 A | 1/1995 | Nakatsuji et al. |
| 6,033,632 A | 3/2000 | Schwartz et al. |

(Continued)

FOREIGN PATENT DOCUMENTS

| CN | 1302781 A | 7/2001 |
| CN | 102030311 A | 4/2011 |

(Continued)

OTHER PUBLICATIONS

Nalbandian et al., "La1-xSrxMO3 (M = Mn, Fe) perovskites as materials for thermochemical hydrogen production in conventional and membrane reactors," International Journal of Hydrogen Energy 34 (2009) 7162-7172.*

(Continued)

*Primary Examiner* — Anthony J Zimmer
(74) *Attorney, Agent, or Firm* — Steinfl + Bruno LLP

(57) ABSTRACT

To provide a catalyst, which is formed from a perovskite oxide, for thermochemical fuel production, and a method of producing fuel using thermochemical fuel production that is capable of allowing a fuel to be produced in a thermochemical manner. Provided is a catalyst for thermochemical fuel production, which is used for producing the fuel from thermal energy by using a two-step thermochemical cycle of a first temperature and a second temperature that is equal to or lower than the first temperature, wherein the catalyst is (Continued)

formed from a perovskite oxide having a compositional formula of $AXO_{3\pm\delta}$ (provided that, $0\leq\delta\leq1$). Here, A represents one or more of a rare-earth element (excluding Ce), an alkaline earth metal element, and an alkali metal element, X represents one or more of a transition metal element and a metalloid element, and O represents oxygen.

4 Claims, 10 Drawing Sheets

Related U.S. Application Data

(60) Provisional application No. 61/615,122, filed on Mar. 23, 2012.

(51) Int. Cl.

| | | |
|---|---|---|
| B01J 37/08 | (2006.01) | |
| B01J 23/00 | (2006.01) | |
| B01J 23/83 | (2006.01) | |
| B01J 35/00 | (2006.01) | |
| C01B 3/06 | (2006.01) | |
| C01B 13/02 | (2006.01) | |
| C07C 29/159 | (2006.01) | |
| B01J 23/26 | (2006.01) | |
| C01B 3/04 | (2006.01) | |
| C07C 1/20 | (2006.01) | |

(52) U.S. Cl.
CPC ............ *B01J 23/34* (2013.01); *B01J 23/83* (2013.01); *B01J 35/002* (2013.01); *B01J 37/08* (2013.01); *C01B 3/045* (2013.01); *C01B 3/063* (2013.01); *C01B 13/024* (2013.01); *C07C 1/20* (2013.01); *C07C 29/159* (2013.01); *B01J 2523/00* (2013.01); *C01B 2203/0277* (2013.01); *C01B 2203/0805* (2013.01); *C01B 2203/1088* (2013.01); *C07C 2523/26* (2013.01); *C07C 2523/34* (2013.01); *C07C 2523/889* (2013.01); *Y02E 60/364* (2013.01); *Y02P 20/129* (2015.11); *Y02P 20/134* (2015.11); *Y02P 20/52* (2015.11)

(58) Field of Classification Search
CPC ......... B01J 23/34; B01J 2523/00; C07C 1/20; C07C 29/159; C07C 2523/889; C07C 2523/34; C07C 2523/26; C01B 3/045; C01B 3/063; C01B 13/024; C01B 2203/0277; C01B 2203/0805; C01B 2203/1088; Y02E 60/364; Y02P 20/134; Y02P 20/129
See application file for complete search history.

(56) References Cited

U.S. PATENT DOCUMENTS

| | | |
|---|---|---|
| 6,214,757 B1 | 4/2001 | Schwartz et al. |
| 2005/0245391 A1 | 11/2005 | Tanaka et al. |
| 2007/0105715 A1 | 5/2007 | Suda et al. |
| 2009/0107044 A1 | 4/2009 | Haile et al. |
| 2010/0278709 A1 | 11/2010 | Waller et al. |
| 2011/0082030 A1 | 4/2011 | Kim et al. |
| 2011/0108435 A1* | 5/2011 | Karni ................. C01B 3/04 205/628 |
| 2011/0297666 A1 | 12/2011 | Ihle et al. |
| 2011/0300064 A1* | 12/2011 | Takeshima .......... B01J 23/002 423/657 |

FOREIGN PATENT DOCUMENTS

| | | |
|---|---|---|
| JP | 2004/269296 | 9/2004 |
| JP | 2009/263165 | 11/2009 |

OTHER PUBLICATIONS

Evdou A, et al., $La_{(1-x)}SR_x MnO_{3-\delta}$ perovskites as redox materials for the production of high purity hydrogen, Int. J. Hydrogen Energy, 2008, vol. 33, p. 5554-5562, ABSTRACT.
International Search Report for PCT Application No. PCT/JP2013/058431 dated Jun. 25, 2013.
Kindermann et al., "Chemical Interactions between La—Sr—Mn—Fe—0 Based Perovskites and Yttria-Stabilized Zirconia," J. Am. Chem. Soc., 80 [4] 909-14 (1997).
Keith et al., "Synthesis, Crystal Structure, and Characterization of Ba(Ti1 /2Mn1 /2)03: A High Permittivity 12R-Type Hexagonal Perovskite," Chem. Mater. 2004, 16, 2007-2015.
Langhammer et al., "Crystal Structure and Related Properties of Manganese-Doped Barium Titanate Ceramics," J. Am. Chem. Soc., 83 [3] 605-11 (2000).
Restriction Requirement dated Feb. 13, 2014 for U.S. Appl. No. 13/600,948 filed Aug. 31, 2012 in the name of Yoshihiro Yamazaki.
Non-Final Office Action dated Jul. 14, 2014 for U.S. Appl. No. 13/600,948 filed Aug. 31, 2012 in the name of Yoshihiro Yamazaki.
Zhang, H. et al. "Effect of Partial Substitution for A, B Sites of Perovskite-Type Oxides Containing Cobalt on Oxygen Desorption and Catalytic Activity" Journal of Catalysis, vol. 13, No. 6, Nov. 30, 1992, pp. 432-437, English translation included.
Li, P. et al. "The Effects of Crystal Structure and Electronic Structure on Photocatalytic $H_2$ Evolution and $CO_2$ Reduction over Two Phases of Perovskite-Structured $NaNbO_3$" The Journal of Physical Chemistry C. vol. 116, Mar. 11, 2012, pp. 7621-7628.
Mawdsley et al. "Rare earth-first-row transition metal perovskites as catalysts for the autothermal reforming of hydrocarbon fuels to generate hydrogen" Applied Catalysis A: General, vol. 334, Oct. 25, 2007, pp. 311-320.
Third Office Action for Chinese Patent Application No. 201380015007.4 filed on behalf of Japan Science and Technology Agency et al. dated Dec. 13, 2016. 24 pages. (Chinese original + English translation).
Nalbandian, L. et al. "La1-xSrxMyFe1-yO3-[delta] perovskites as oxygen-carrier materials for chemical-looping reforming" International Journal of Hydrogen Energy. vol. 36, No. 11, Feb. 2011, pp. 6657-6670.
Mori, M. "Effect of B-site doing on thermal cycle shrinkage for La0.8Sr0.2Mn1-xMxO3+[delta] perovskites (M=Mg, Al, Ti, Mn, Fe, Co, Ni; $0\leq x\leq 0.1$)" Solid State Ionics vol. 174, No. 1-4, (Oct. 2004) pp. 1-8.
European Patent Office Search Report for Application No. EP 13764774.9 filed Jan. 28, 2015 on behalf of Japan Science & Technology Agency et al. dated Dec. 15, 2015.
Leion, H. et al. "Use of $CaMn_{0.875}Ti_{0.125}O_3$ as Oxygen Carrier in Chemical-Looping with Oxygen Uncoupling" Energy Fuels; 2009; vol. 23; pp. 5276-5283.
Ryden, M. et al. "$CaMn_{0.875}Ti_{0.125}O_3$ as oxygen carrier for chemical-looping combustion with oxygen uncoupling (CLOU)-Experiments in a continuously operating fluidized-bed reactor system" International Journal of Greenhouse Gas Control; 2011; vol. 5; pp. 356-366.
Thursfield, A. et al. "Chemical looping and oxygen permeable ceramic membranes for hydrogen production—a review" Energy & Environmental Science; 2012; vol. 5; pp. 7421-7459.
Extended European Search Report for European Patent Application No. 13764774.9 filed on behalf of Japan Science and Technology Agency, et al. dated Apr. 11, 2016; 18 pages.

\* cited by examiner 800-1400 °C

Ba(Ti$_{0.6}$Mn$_{0.4}$)O$_{3\pm\delta}$, 800-1400 °C

La$_{1-x}$Sr$_x$MnO$_{3\pm\delta}$, (x=0, 0.1, 0.2), 800-1500 °C

CATALYSTS FOR THERMOCHEMICAL FUEL PRODUCTION AND METHOD OF PRODUCING FUEL USING THERMOCHEMICAL FUEL PRODUCTION

CROSS REFERENCE TO RELATED APPLICATIONS

This application is a U.S. divisional application of U.S. patent application Ser. No. 13/600,948, filed Aug. 31, 2012, which in turn, claims benefit from U.S. Provisional application Ser. No. 61/615,122, filed Mar. 23, 2012, the contents of both of which are incorporated herein by reference in their entirety.

FEDERAL SUPPORT STATEMENT

This invention was made with government support under Grant No. CBET0829114 awarded by the National Science Foundation. The government has certain rights in the invention.

FIELD

The present invention relates to catalysts for thermochemical fuel production, and a method of producing fuel using thermochemical fuel production.

BACKGROUND

A thermochemical fuel generating method is a technology of producing a chemical fuel from thermal energy that may be obtained from sunlight and the like, and of storing the thermal energy as a chemical fuel. The fuel is produced by a two-step thermal cycle (thermochemical cycle) which includes a step performed under a high temperature (first temperature) and a step performed under a low temperature (second temperature). In practice, when a catalyst oxide is reduced at a high temperature, and carbon dioxide that is a raw material gas, water vapor, and the like are introduced to the reduced catalyst oxide, the catalyst oxide absorbs oxygen from a raw material, and thus fuels such as a syngas, methane, hydrocarbon, alcohol, and hydrogen may be produced.

As oxide-based catalysts, mainly, $ZnO$—$Zn$, $Fe_2O_3$—$FeO$, $CeO_2$—$Ce_2O_3$, $CeO_2$ having a nonstoichiometric composition, mixtures thereof, a partially substituted oxide, and the like have been reported. Water vapor modification of methane ($CH_4+H_2O \rightarrow 6H_2+CO$) using $LaSrMnO_3$-based perovskite oxide has been reported, but this is completely different from thermochemical fuel generation ($H_2O \rightarrow H_2 + \frac{1}{2}O_2$, or $CO_2 \rightarrow CO + \frac{1}{2}O_2$) using water or carbon dioxide, and thermochemical fuel production using a perovskite oxide $AXO_3$ has not been reported until now.

Among fuels that may be generated by the thermochemical fuel generation method, for example, hydrogen is a clean energy source that generates only water after combustion, and thus hydrogen is expected as renewable energy.

When hydrogen is produced by directly decomposing water ($H_2O \rightarrow H_2 + \frac{1}{2}O_2$), a high temperature of several thousands of °C. is necessary, but when using the thermochemical fuel generation method, hydrogen may be produced by decomposing water by a thermal cycle of two-step temperature of relatively low temperature (for example, refer to Japanese unexamined Patent Application, First Publication No. 2004-269296).

In the two-step thermal cycle (thermochemical cycle) which includes a step performed under a high temperature (first temperature) and a step performed under a low temperature (second temperature), with respect to the high temperature heating, a technology using solar energy is known (for example, Japanese Unexamined Patent Application, First Publication No. 2009-263165).

Solar energy is, by far, the most abundant renewable energy source. To fully take advantage of this vast energy source, it must be efficiently stored in a stable form on a massive scale. To store sunlight into chemical forms, solar thermochemical fuel production using nonstoichiometric oxide has been researched. It is a two-step thermochemical cycle that drives redox reaction between the oxide and gas species. The oxide is reduced at a high temperature at which oxygen is released from the oxide. Then, at a lower temperature at which carbon dioxide and/or water vapor are introduced, the oxide strips oxygen atoms from the introduced gas. As a result, syngas, methane, and hydrogen fuels are produced. The thermodynamic efficiency is calculated to be 15 to 75% depending on the oxide systems including $ZnO$—$Zn$, $Fe_2O_3$—$FeO$, $CeO_2$—$Ce_2O_3$, nonstoichiometric $CeO_2$ systems, and some combinations between them. Other systems have been largely unexplored. A record solar-fuel conversion efficiency is 0.8% in a solar-thermochemical cycle of 800 to 1,630° C. using undoped ceria, with 1.3 to 1.5 liters of carbon monoxide and hydrogen production.

As catalyst oxides that are used in the thermochemical fuel generation method, cerium oxide (ceria) is known as indicated in the specification of US Patent Application Publication No. 2009/0107044. In the solar thermochemical efficiency experiment using undoped ceria, the solar reactor lost energy of 50% or less as heat, specifically above 1,250° C., and energy of 40% or less as solar re-reflection from the aperture. Thus, the large improvement in solar-fuel conversion efficiency can be anticipated. To address this issue, a mechanical engineering approach and a materials science approach are possible. A heat recovery system might also be integrated. The challenge in this route is how to choose an appropriate oxide structure as well as materials chemistry process from millions of candidate oxides that might show the desired properties. Combinatorial synthesis might be very useful to make candidate oxides, but a rapid way to check fuel productivity at high temperatures is required.

SUMMARY

An object of the invention is to provide a catalyst, which is formed from a perovskite oxide, for thermochemical fuel production, and a method of producing fuel using thermochemical fuel production that is capable of allowing a fuel to be produced in a thermochemical manner.

The invention proposes catalysts for thermochemical fuel production, particularly, bio-inspired catalytic perovskite for solar thermochemical water splitting. Natural photosynthesis, specifically, water oxidation is catalyzed in the $Mn_4CaO_5$ cluster that possesses the cubic-like frame with a projection. It is anticipated that the artificial water splitting might occur in a similar cubic-like structure containing manganese elements. This hypothesis led to the thermochemical water splitting experiment using manganese-based perovskite (a cubic-like structure, a structure shown on the right of graph in FIG. 3). The perovskite splits water and produces hydrogen with the amount exceeding the amount of hydrogen the ceria produces. As far as the present inventors know, this is the first demonstration of thermochemical water splitting using nonstoichiometric perovskite oxides. The Sr-doped LaMnO$_3$ perovskites were utilized in the steam reforming of methane, but no thermochemical water splitting has been demonstrated in perovskite oxides. The black color of the perovskite, compared with the white color of ceria, would be beneficial in efficient solar absorbance, thus making possible efficient solar-fuel conversion.

The two-step thermochemical cycle reaction, which uses the perovskite oxide as catalyst for hydrogen production as an example of the catalyst for the thermochemical fuel production, includes the following two steps of an oxygen releasing reaction and a hydrogen generating reaction.

$$AXO_3 \rightarrow AXO_{3\pm\delta} + (\delta/2)O_2 \quad \text{[Oxygen Releasing Reaction (High-Temperature Reduction Reaction)]}$$

$$AXO_{3\pm\delta}\delta H_2O \rightarrow AXO_3\delta H_2 \quad \text{[Hydrogen Generating Reaction (Low-Temperature Oxidation Reaction)]}$$

In addition, the entire reaction is represented as follows.

$$\delta H_2O \rightarrow \delta H_2 + (\delta/2)O_2 \quad \text{[Entire Reaction]}$$

In addition, the two-step thermochemical cycle reaction, which uses the perovskite oxide as a catalyst for thermochemical methane production as an example of the catalyst for the thermochemical fuel production, includes the following two steps of an oxygen releasing reaction and a methane generating reaction.

$$AXO_3 \rightarrow AXO_{3\pm\delta} + (\delta/2)O_2 \quad \text{[Oxygen Releasing Reaction (High-Temperature Reduction Reaction)]}$$

$$AXO_{3\pm\delta} + (\delta/4)CO_2 + (\delta/2)H_2O \rightarrow AXO_3 + (\delta/4)CH_4 \quad \text{[Methane Generating Reaction (Low-Temperature Oxidation Reaction)]}$$

In addition, the entire reaction is represented as follows.

$$(\delta/4)CO_2 + (\delta/2)H_2O \rightarrow (\delta/4)CH_4 + (\delta/2)O_2 \quad \text{[Entire Reaction]}$$

In addition, the two-step thermochemical cycle reaction, which uses the perovskite oxide as a catalyst for thermochemical methanol production as an example of the catalyst for the thermochemical fuel production, includes the following two steps of an oxygen releasing reaction and a methane generating reaction.

$$AXO_3 \rightarrow AXO_{3\pm\delta} + (\delta/2)O_2 \quad \text{[Oxygen Releasing Reaction (High-Temperature Reduction Reaction)]}$$

$$AXO_{3\pm\delta} + (\delta/3)CO_2 + (2\delta/3)H_2O \rightarrow AXO_3 + (\delta/3)CH_3OH \quad \text{[Methanol Generating Reaction (Low-Temperature Oxidation Reaction)]}$$

In addition, the entire reaction is represented as follows.

$$(\delta/3)CO_2 + (2\delta/3)H_2O \rightarrow (\delta/3)CH_3OH + (\delta/2)O_2 \quad \text{[Entire Reaction]}$$

To accomplish the above-described object, the invention provides the following means.

(1) A catalyst for thermochemical fuel production, which is used for producing the fuel from thermal energy by using a two-step thermochemical cycle of a first temperature and a second temperature that is equal to or lower than the first temperature, wherein the catalyst is formed from a perovskite oxide having a compositional formula of $AXO_{3\pm\delta}$ (provided that, $0 \leq \delta < 1$). Here, A represents one or more of a rare-earth element (excluding Ce), an alkaline earth metal element, and an alkali metal element, X represents one or more of a transition metal element and a metalloid element, and O represents oxygen.

(2) The catalyst for thermochemical fuel production according to (1), wherein the element A is one or more selected from a group consisting of La, Mg, Ca, Sr, and Ba, and the element X is one or more selected from a group consisting of Mn, Fe, Ti, Zr, V, Cr, Co, Ni, Cu, Zn, Mg, Al, Ga, In, C, Si, Ge, and Sn.

(3) The catalyst for thermochemical fuel production according to (2), wherein the element A is La, and the element X is Mn.

(4) The catalyst for thermochemical fuel production according to (3), wherein the element A is partially substituted with one or more of Sr, Ca, and Ba.

(5) The catalyst for thermochemical fuel production according to (3), wherein the element X is partially substituted with one or more of Fe, Ni, V, Cr, Sc, Ti, Co, Cu, and Zn.

(6) The catalyst for thermochemical fuel production according to (1), wherein the element A is La, the element X is Mn, La is partially substituted with Sr.

(7) The catalyst for thermochemical fuel production according to (6), wherein the substituted concentration (x; x represents an amount with an amount of La before substitution being set to 1) of Sr is 0.1 or more to less than 1.0.

(8) The catalyst for thermochemical fuel production according to (7), wherein Mn is partially substituted with Fe.

(9) The catalyst for thermochemical fuel production according to (8), wherein the substituted concentration (x; x represents an amount with an amount of Mn before substitution being set to 1) of Fe is 0.35 or more to 0.85 or less.

(10) The catalyst for thermochemical fuel production according to (1), wherein the element A is Ba, the element X is Ti, Ti is partially substituted with Mn.

(11) The catalyst for thermochemical fuel production according to (10), wherein the substituted concentration (x; x represents an amount with an amount of Ti before substitution being set to 1) of Mn is more than 0 to 0.5 or less.

(12) A method of producing fuel using thermochemical fuel production, wherein the catalyst for thermochemical fuel production according to any one of (1) to (11) is used.

(13) A method of producing fuel using thermochemical fuel production, which produces the fuel from thermal energy by using the catalyst for thermochemical fuel production according to any one of (1) to (11) and by using a two-step thermochemical cycle of a first temperature and a second temperature that is equal to or lower than the first temperature, wherein the first temperature is 600 to 1,600° C., and the second temperature is 400 to 1,600° C.

(14) The method of producing fuel using thermochemical fuel production according to (13), wherein the first temperature is attained by irradiation of condensed sunlight energy and heating, or by heating using waste heat.

(15) A method of producing fuel using thermochemical fuel production, which produces the fuel from thermal energy by using a two-step thermochemical cycle of a first temperature and a second temperature that is equal to or lower than the first temperature, the method including: a process of heating a perovskite oxide having a compositional formula of $AXO_{3\pm\delta}$ (provided that, $0 \leq \delta < 1$) to the first temperature to reduce the perovskite oxide; and a process of bringing a raw material gas into contact with the reduced perovskite oxide and oxidizing the perovskite oxide to produce the fuel.

(16) The method of producing fuel using thermochemical fuel production according to (15), wherein the fuel is any one of hydrogen, methane, and methanol.

(17) The method of producing fuel using thermochemical fuel production according to (15), wherein the raw material gas includes water vapor.

(18) The method of producing fuel using thermochemical fuel production according to (15), wherein the raw material gas includes carbon dioxide and water vapor.

In addition, in this specification, the "thermochemical fuel production" is a concept broadly extending to a concept of "thermochemical hydrogen production" in which water is decomposed into oxygen and hydrogen in relatively mild thermal conditions by combination of a plurality of chemical reactions to fuels including hydrogen.

In addition, the case of "partially substituted with" is that in which the concentration (x) of the substituted element is in the range of more than 0 to less than 1 when the amount of the element to be substituted before substitution is set to 1.

In addition, even when the "second temperature" is the same as the "first temperature", thermochemical fuel production is possible by changing an atmosphere, but in a case where the atmosphere is the same in each case, the "second temperature" represents a temperature lower than the "first temperature".

In addition, in regard to "$\delta$" in the "compositional formula $AXO_{3\pm\delta}$ (provided that, $0 \leq \delta < 1$)", it is preferable that $0 \leq \delta \leq 0.5$, more preferably $0 \leq \delta \leq 0.3$, and still more preferably $0 \leq \delta \leq 0.2$.

According to the invention, it is possible to provide a catalyst, which is formed from a perovskite oxide, for thermochemical fuel production, and a method of producing fuel using thermochemical fuel production that is capable of allowing a fuel to be produced in a thermochemical manner.

The present invention provides a new catalyst for thermochemical fuel production by using perovskite oxide $AXO_3$.

According to the invention, elements such as iron and manganese, which are, at present, abundantly found in the Earth's crust, are used, and thus the used amount of rare-earth elements may be reduced. Therefore, it is possible to provide a catalyst for thermochemical fuel production and a method of producing fuel using thermochemical fuel production, in which significant cost reduction may be anticipated, and this will enable the conversion of solar energy into chemical fuel in high efficiency and the storage thereof.

DETAILED DESCRIPTION

Figure 1:
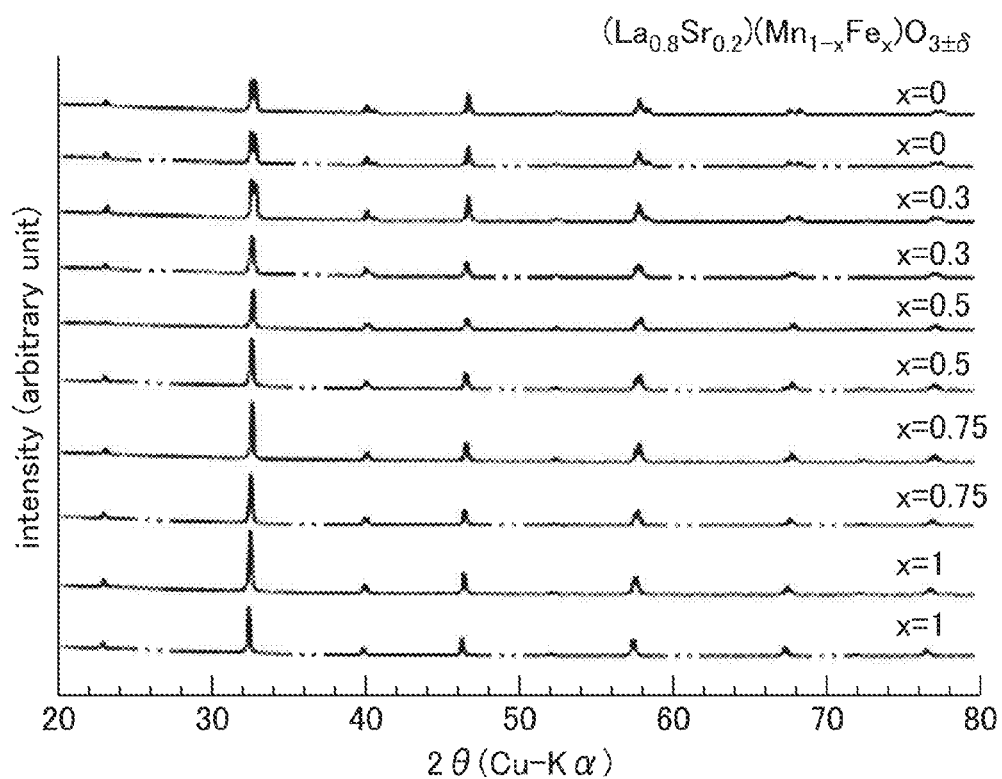
FIG. 1 is a graph illustrating X-ray diffraction results of $La_{0.8}Sr_{0.2}Mn_{1-x}Fe_xO_{3\pm\delta}$ (x=0 to 1).

Hereinafter, a catalyst for thermochemical fuel production and a method of producing fuel using thermochemical fuel production, to which the invention is applied, will be described with reference to the attached drawings. In addition, in the drawings that are used in the following description, characteristic portions are sometimes enlarged for easy understanding of the characteristics, and the ratio of dimensions or the like of each constituent element is not limited to an actual value. In addition, in the following description, exemplified examples are for illustrative purposes only, and the invention is not limited thereto, and may be executed in a state of being appropriately changed without departing from a gist of the invention.

The catalyst for thermochemical fuel production according to the invention is a catalyst for thermochemical fuel production, which is used for producing the fuel from thermal energy by using a two-step thermochemical cycle of a first temperature and a second temperature that is equal to or lower than the first temperature. The catalyst is formed from a perovskite oxide having a compositional formula of $AXO_{3\pm\delta}$ (provided that, $0 \leq \delta < 1$). Here, A represents one or more of a rare-earth element (excluding Ce), an alkaline earth metal element, and an alkali metal element, X represents one or more of a transition metal element and a metalloid (semi-metallic) element, and O represents oxygen.

A value of $\delta$ may be determined in a range not deteriorating an effect of the invention.

Examples of the rare-earth element (excluding Ce) include Sc (scandium), Y (yttrium), La (lanthanum), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), Lu (lutetium), and the like.

Examples of the alkaline earth metal element include Be (beryllium), Mg (magnesium), Ca (calcium), Sr (strontium), Ba (barium), and Ra (radium).

Examples of the alkali metal include Li (lithium), Na (sodium), K (potassium), Rb (rubidium), Cs (cesium), and Fr (francium).

Examples of the transition metal element include first transition elements (3d transition elements) such as Sc (scandium), Ti (titanium), V (vanadium), Cr (chromium), Mn (manganese), Fe (iron), Co (cobalt), Ni (nickel), Cu (copper), and Zn (zinc), second transition elements (4d transition elements) such as Y (yttrium), Zr (zirconium), Nb (niobium), Mo (molybdenum), Tc (technetium), Ru (ruthenium), Rh (rhodium), Pd (palladium), Ag (silver), and Cd (cadmium), and third transition elements (4f transition elements) such as La (lanthanum), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), Lu (lutetium), Hf (hafnium), Ta (tantalum), W (tungsten), Re (rhenium), Os (osmium), Ir (iridium), Pt (platinum), and Au (gold).

Examples of the metalloid element include B (boron), Si (silicon), Ge (germanium), As (arsenic), Sb (antimony), Te (tellurium), Se (selenium), Po (polonium), and At (astatine).

A method of producing fuel using thermochemical fuel production according to an embodiment of the invention is a method of producing fuel using thermochemical fuel production, which produces the fuel from thermal energy by using the catalyst for thermochemical fuel production of the invention and by using a two-step thermochemical cycle of a first temperature and a second temperature that is equal to or lower than the first temperature. The first temperature is 600 to 1,600° C., and the second temperature is 400 to 1,600° C.

The first temperature and/or the second temperature are attained, for example, by irradiation of condensed sunlight energy and heating, or by heating using waste heat.

As the "waste heat", for example, waste heat of a power generator, a blast furnace, and the like may be used.

In the case of producing hydrogen as a fuel, the first temperature may be set to 600 to 1,600° C. (for example, 1,400° C.), and the second temperature may be set to 400 to 1,600° C. (for example, 800° C.).

In the case of producing methane as a fuel, the first temperature may be set to 600 to 1,600° C. (for example, 1,400° C.), and the second temperature may be set to 300 to 1,600° C. (for example, 450° C.).

In the case of producing methanol as a fuel, the first temperature may be set to 600 to 1,600° C. (for example, 1,400° C.), and the second temperature may be set to 200 to 1,600° C. (for example, 350° C.).

A method of producing fuel using thermochemical fuel production according to another embodiment of the invention is a method of producing fuel using thermochemical fuel production, which produces the fuel from thermal energy by using a two-step thermochemical cycle of a first temperature and a second temperature that is equal to or lower than the first temperature. The method includes a process of heating a perovskite oxide having a compositional formula of $AXO_{3\pm\delta}$ (provided that, $0 \leq \delta < 1$) to the first temperature to reduce the perovskite oxide, and a process of bringing a raw material gas into contact with the reduced perovskite oxide and oxidizing the perovskite oxide to produce the fuel.

A value of $\delta$ may be determined in a range not deteriorating an effect of the invention.

Examples of the fuel, which may be produced by the method of producing fuel using thermochemical fuel production of the invention, include hydrogen, methane, and methanol, but are not limited thereto.

As an example of the raw material gas, for example, water vapor may be exemplified, but it is not limited thereto. Hydrogen may be produced by using the water vapor. In addition, as other examples, carbon dioxide and water vapor may be exemplified. Methane or methanol may be produced by using carbon dioxide and water vapor.

First, an outline of a method of producing a catalyst for thermochemical hydrogen production, as an example of the catalyst for thermochemical fuel production of the invention, will be described.

In the production of the catalyst for thermochemical hydrogen, a known method of producing perovskite oxide may be used. For example, powders of raw materials (oxide, hydroxide, oxide-hydroxide, and the like) including elements of a desired perovskite oxide are weighed to obtain a target compositional ratio, and are mixed and crushed. Then, the resultant mixture is calcined, and then the resultant calcined material is fired to produce the catalyst for producing thermochemical hydrogen.

More specifically, an example of a method of producing $La_{0.8}Sr_{0.2}Mn_{1-x}Fe_xO_{3\pm\delta}$ will be described.

Porous pellet of $La_{0.8}Sr_{0.2}Mn_{1-x}Fe_xO_{3\pm\delta}$ were synthesized via solid-state reaction. First, raw material oxides ($La_2O_3$, $SrCO_3$, $MnCO_3$, and $Fe_2O_3$) were crushed using an attritor-milling and were calcined at 1,000° C. for three hours in air. These powders, that were obtained, were put into a die with isopropanol and were sintered at 1,500° C. for 10 hours to obtain the porous pellets.

It was confirmed that the pellet of $La_{0.8}Sr_{0.2}Mn_{1-x}Fe_xO_{3\pm\delta}$ had a perovskite structure by X-ray diffraction (refer to FIG. 1). The resultant porosity of the pellet was approximately 60%. In addition, it was verified that the resultant pellets had various sizes of pores, ranging from a few to over 100 μm from a secondary electron microscopy image (refer to FIG. 2).

Next, an outline of production of hydrogen by using the catalyst for thermochemical hydrogen production that was obtained will be described.

For example, the production of hydrogen may be carried out as described below by using the catalyst for thermochemical hydrogen production.

Figure 3:
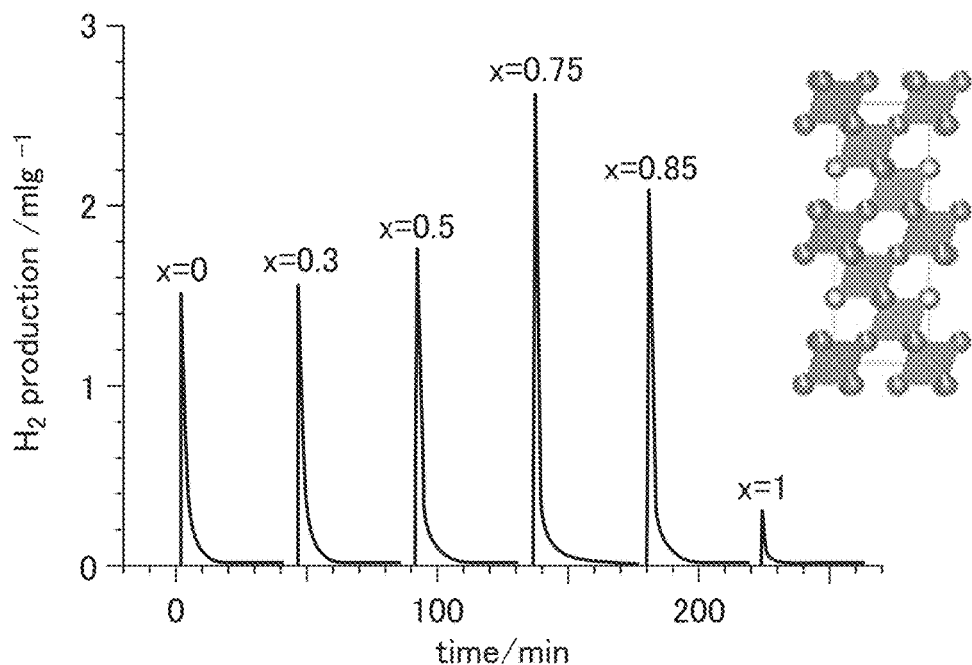
FIG. 3 is a graph illustrating a hydrogen production amount in the case of using $La_{0.8}Sr_{0.2}Mn_{1-x}Fe_xO_{3\pm\delta}$ as a catalyst for thermochemical fuel (hydrogen) production.

The porous pallet was placed inside an infrared furnace and was heated up to 1,400° C. (corresponding to the "first temperature" of the two-step thermochemical cycle) in dry nitrogen containing 10 ppm of oxygen. At this time, it was observed that oxygen was released from the pellet by using mass spectroscopy. Then, the pellet was cooled down to 800° C. (corresponding to the "second temperature" of the two-step thermochemical cycle), followed by flowing 10% water vapor containing argon gas. Hydrogen evolution was observed at 800° C. with an amount of 3 ml/g (corresponding to 60% or less of a hydrogen evolution amount in the case of using undoped ceria). The hydrogen evolution reaction was completed within 10 minutes as shown in FIG. 3.

Figure 4:
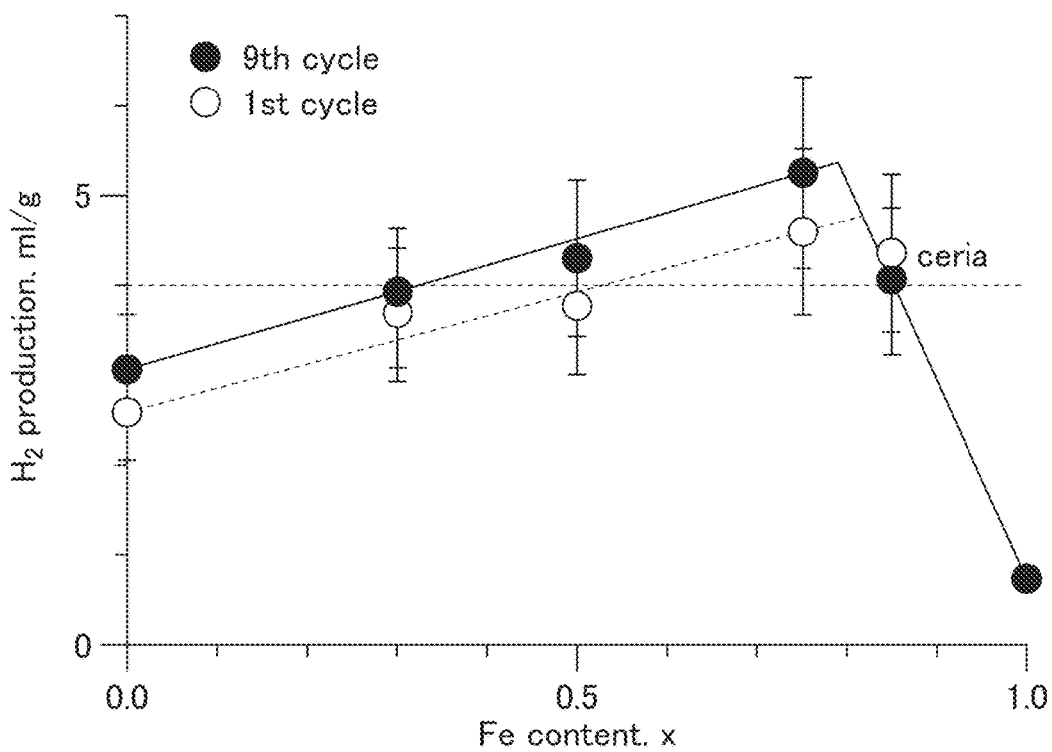
FIG. 4 is a graph illustrating dependency of a hydrogen production (generation) amount on an iron concentration (x) in the case of using $La_{0.8}Sr_{0.2}Mn_{1-x}Fe_xO_{3\pm\delta}$ as a catalyst for thermochemical fuel (hydrogen) production.

The hydrogen evolution was reproducible over 9 cycles with slight increase in the amount, as shown in FIG. 4.

As an attempt to obtain more covalent (relatively weaker) metal-oxygen bonds in the octahedral perovskite, $La_{0.8}Sr_{0.2}Mn_{1-x}Fe_xO_{3\pm\delta}$ in which manganese is partially replaced with iron that has a higher electronegativity in the valence bond theory was synthesized. Analysis results of $La_{0.8}Sr_{0.2}Mn_{1-x}Fe_xO_{3\pm\delta}$ are shown below.

FIG. 1 shows a graph illustrating X-ray diffraction results of $La_{0.8}Sr_{0.2}Mn_{1-x}Fe_xO_{3\pm\delta}$. X represents a concentration of Fe (that is an amount when an amount of Mn before substitution is set to 1), and X-ray diffraction results are shown in the case of x=0 (corresponding to a case of not containing Fe), in the case of x=0.3 (30 at %), in the case of x=0.5 (50 at %), in the case of x=0.75 (75 at %), and in the case of x=1 (100 at %; a case in which Mn atoms are entirely substituted with Fe atoms). As shown in FIG. 1, the perovskite structure is maintained at the entire iron concentrations (x) of $La_{0.8}Sr_{0.2}Mn_{1-x}Fe_xO_{3\pm\delta}$. Differential scanning calorimetry also showed no evidence in phase transformation up to 1,400° C.

In addition, bold lines represent results before a thermal cycle and narrow lines represent results after the thermal cycle, and it can be seen that all of these show a perovskite structure.

Figure 2:
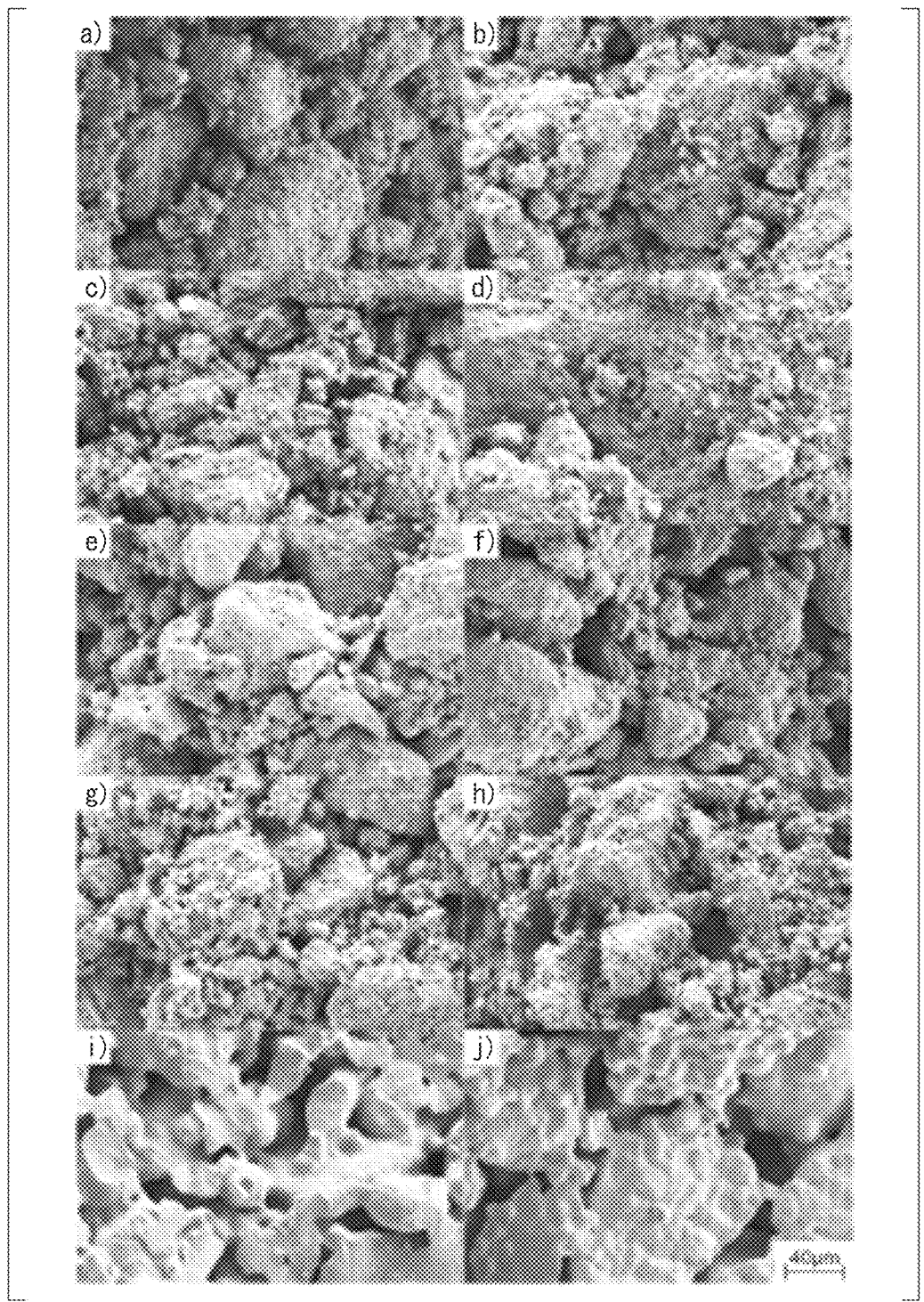
FIG. 2 is secondary electron microscope photographs of $La_{0.8}Sr_{0.2}Mn_{1-x}Fe_xO_{3\pm\delta}$.

FIG. 2 shows secondary electron microscope photographs of $La_{0.8}Sr_{0.2}Mn_{1-x}Fe_xO_{3\pm\delta}$. In the drawing, (a), (c), (e), (g), and (i) represent the secondary electron microscope photographs before the thermal cycle, and (b), (d), (f), (h), and (j) represent the secondary electron microscope photographs after the thermal cycle of 800 to 1400° C. In (a) and (b), the iron concentration x is 0, in (c) and (d), the iron concentration x is 0.3, in (e) and (f), the iron concentration x is 0.5, in (g) and (h), the iron concentration x is 0.75, and in (i) and (j), the iron concentration x is 1.

It can be seen that the porous structure is maintained after the thermal cycle in any specimen.

FIG. 3 shows a graph illustrating a hydrogen production amount in the case of using $La_{0.8}Sr_{0.2}Mn_{1-x}Fe_xO_{3\pm\delta}$ as a catalyst for thermochemical hydrogen production. The first temperature and the second temperature of the thermal (thermochemical) cycle were 1,400° C. and 800° C., respectively.

As shown in FIG. 3, as the content of Fe increased in the order of the case in which the concentration (x) of iron (Fe) was 0 (corresponding to the case of not containing Fe), the case of x=0.3 (30 at %), the case of x=0.5 (50 at %), and the case of x=0.75 (75 at %), the hydrogen production amount increased, and the hydrogen production amount in the case in which x is 0.75 was approximately 1.6 times the case of not containing Fe (x=0). The hydrogen production amount in the case of x=0.85 (85 at %) decreased by 15% compared to the case of x=0.75. In a case in which all of the Mn atoms were substituted with Fe atoms (x=1), the hydrogen production amount was approximately 10% of that of the case of x=0.75.

In the case of using $La_{0.6}Sr_{0.4}MnO_{3\pm\delta}$ as a catalyst for thermochemical hydrogen production, in which the first temperature and the second temperature of the thermal (thermochemical) cycle were 1,400° C. and 800° C., respectively, the hydrogen production amount was 7.5 ml/g.

FIG. 4 shows a graph illustrating dependency of a hydrogen production (generation) amount on an iron concentration (x) in the case of using $La_{0.8}Sr_{0.2}Mn_{1-x}Fe_xO_{3\pm\delta}$ as a catalyst for thermochemical hydrogen production. The first temperature and the second temperature of the thermal cycle were 1,400° C. and 800° C., respectively.

Results indicated by a white circle represent first cycle results, and results indicated by a black circle represent ninth cycle results.

As shown in FIG. 4, the hydrogen production amount in a case where x is 0.35 to 0.85 was larger than a hydrogen production amount (4.0 mg/l) of ceria, and the hydrogen production amount in the case of x=0.75 was 5.3 mg/l and was larger than the hydrogen production amount of ceria by 30% or more.

Figure 5:
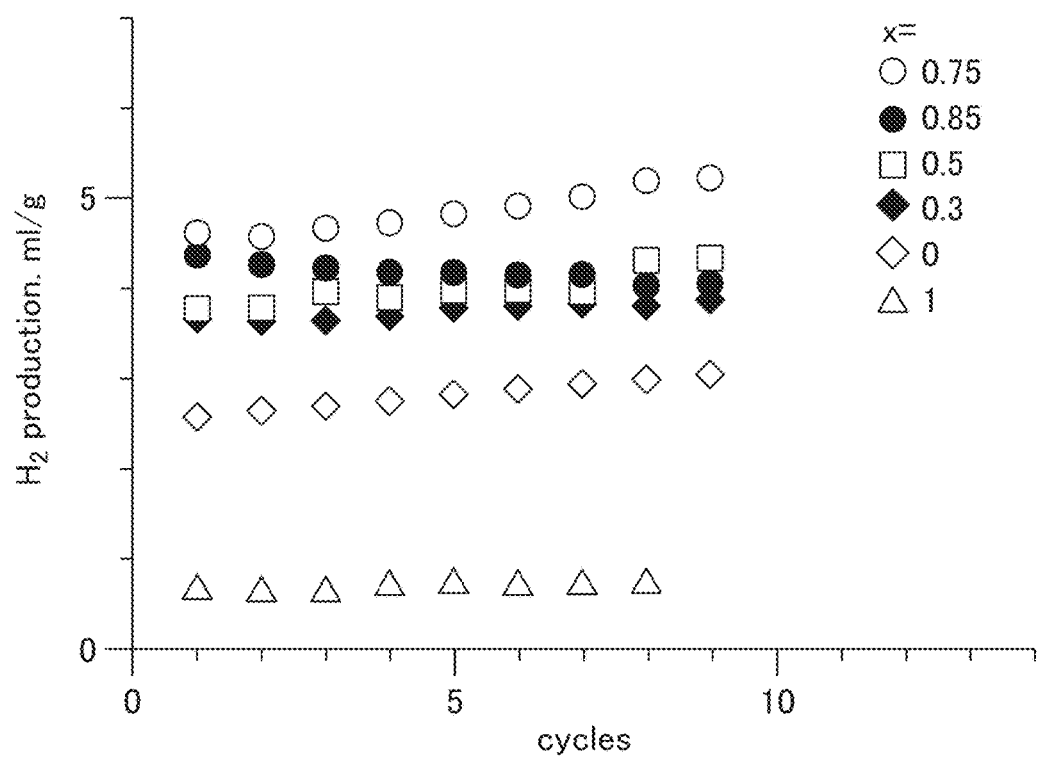
FIG. 5 is a graph illustrating a cycle characteristic of the hydrogen production amount in the case of using $La_{0.8}Sr_{0.2}Mn_{1-x}Fe_xO_{3\pm\delta}$.

FIG. 5 shows a graph illustrating a cycle characteristic of the hydrogen production amount in the case of using $La_{0.8}Sr_{0.2}Mn_{1-x}Fe_xO_{3\pm\delta}$ as the catalyst for thermochemical hydrogen production. The first temperature and the second temperature of the thermal cycle were 1,400° C. and 800° C., respectively.

In a case where the iron concentration x is 0, 0.3, 0.5, 0.75, and 1, the hydrogen production amount gradually increased with the cycle. In a case of the iron concentration x=0.85, the hydrogen production amount gradually decreased with the cycle. In addition, although not shown in FIG. 5, the hydrogen production amount became constant at fifteen cycles.

A cycle characteristic, which is stable in any case without being dependent upon the iron concentration, was obtained.

Figure 6A:
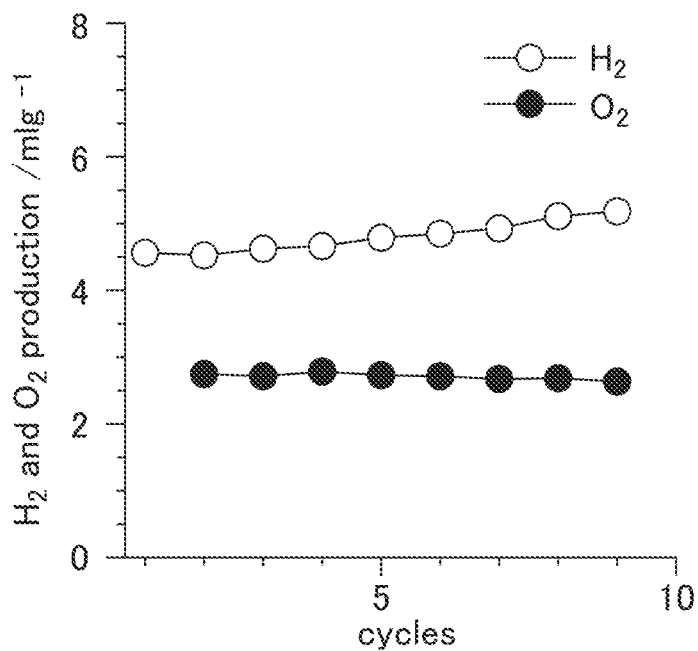
FIG. 6A is a graph illustrating a cycle characteristic of the hydrogen production amount and an oxygen production amount in the case of using $La_{0.8}Sr_{0.2}Mn_{1-x}Fe_xO_{3\pm\delta}$.
Figure 6B:
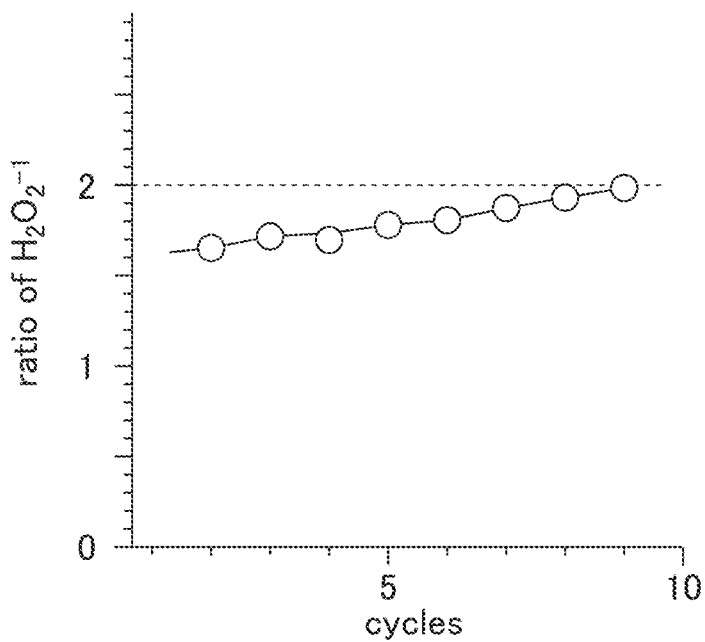
FIG. 6B is a graph illustrating a cycle characteristic of the hydrogen production amount and the oxygen production amount.

FIG. 6A shows a graph illustrating a cycle characteristic of the hydrogen production amount and the oxygen production amount in the case of using $La_{0.8}Sr_{0.2}Mn_{1-x}Fe_xO_{3\pm\delta}$, and FIG. 6B shows a graph illustrating a cycle characteristic of the hydrogen production amount and the oxygen production amount. The first temperature and the second temperature of the thermal cycle were 1,400° C. and 800° C., respectively.

As shown in FIG. 6B, a ratio ($H_2$ amount/$O_2$ amount) of the hydrogen production amount and the oxygen production amount is approximately two, and FIG. 6B shows results of water splitting.

Figure 7:
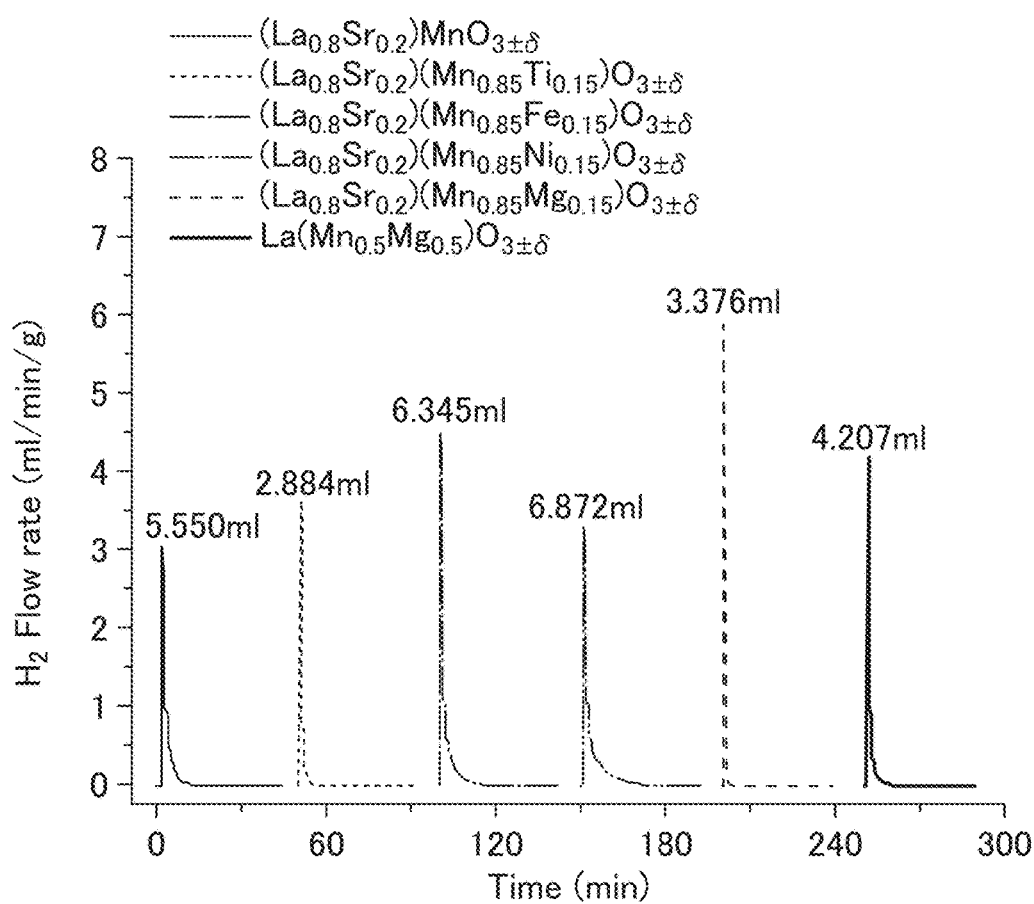
FIG. 7 is a graph illustrating a hydrogen production amount in the case of using $(La_{0.8}Sr_{0.2})MnO_{3\pm\delta}$, $(La_{0.8}Sr_{0.2})(Mn_{0.85}Ti_{0.15})O_{3\pm\delta}$, $(La_{0.8}Sr_{0.2})(Mn_{0.85}Fe_{0.15})O_{3\pm\delta}$, $(La_{0.8}Sr_{0.2})(Mn_{0.85}Ni_{0.15})O_{3\pm\delta}$, $(La_{0.8}Sr_{0.2})(Mn_{0.85}Mg_{0.85})O_{3\pm\delta}$, and $La(Mn_{0.5}Mg_{0.5})O_{3\pm\delta}$ as a catalyst for thermochemical hydrogen production, respectively.

FIG. 7 shows a graph illustrating a hydrogen production amount in the case of Using $(La_{0.8}Sr_{0.2})MnO_{3\pm\delta}$, $(La_{0.8}Sr_{0.2})(Mn_{0.85}Ti_{0.15})O_{3\pm\delta}$, $(La_{0.8}Sr_{0.2})(Mn_{0.85}Fe_{0.15})O_{3\pm\delta}$, $(La_{0.8}Sr_{0.2})(Mn_{0.85}Ni_{0.15})O_{3\pm\delta}$, $(La_{0.8}Sr_{0.2})(Mn_{0.85}Mg_{0.15})O_{3\pm\delta}$, and $La(Mn_{0.5}Mg_{0.5})O_{3\pm\delta}$ as a catalyst for thermochemical hydrogen production. The hydrogen production amount is indicated by a flow rate (ml/min/g) per unit gram. The first temperature and the second temperature of the thermal (thermochemical) cycle were 1,400° C. and 800° C.

As shown in FIG. 7, even when perovskite oxide in which an A site is allocated to La, or La and Sr, and an X site is allocated to Mn, or Mn and at least one of Ti, Fe, Ni, and Mg is used in the catalyst for thermochemical hydrogen production, hydrogen may be produced in a thermochemical manner.

Figure 8:
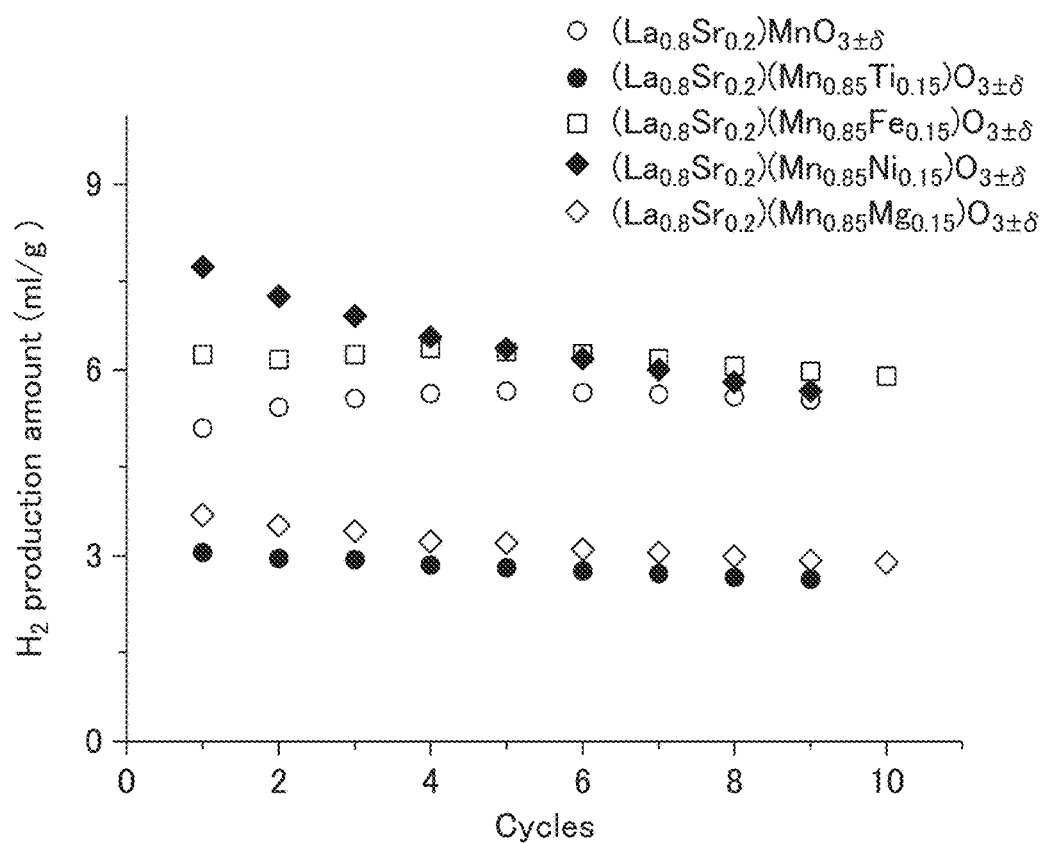
FIG. 8 is a graph illustrating a cycle characteristic of the hydrogen production amount in the case of using $(La_{0.8}Sr_{0.2})MnO_{3\pm\delta}$, $(La_{0.8}Sr_{0.2})(Mn_{0.85}Ti_{0.5})O_{3\pm\delta}$, $(La_{0.8}Sr_{0.2})(Mn_{0.85}Fe_{0.5})O_{3\pm\delta}$, $(La_{0.8}Sr_{0.2})(Mn_{0.85}Ni_{0.15})O_{3\pm\delta}$, and $(La_{0.8}Sr_{0.2})(Mn_{0.85}Mg_{0.5})O_{3\pm\delta}$ as a catalyst for producing thermochemical hydrogen, respectively.

FIG. 8 shows a graph illustrating a cycle characteristic of the hydrogen production amount in the case of using $(La_{0.8}Sr_{0.2})MnO_{3\pm\delta}$, $(La_{0.8}Sr_{0.2})(Mn_{0.85}Ti_{0.15})O_{3\pm\delta}$, $(La_{0.8}Sr_{0.2})(Mn_{0.85}Fe_{0.5})O_{3\pm\delta}$, $(La_{0.8}Sr_{0.2})(Mn_{0.85}Ni_{0.15})O_{3\pm\delta}$, and $(La_{0.8}Sr_{0.2})(Mn_{0.85}Mg_{0.15})O_{3\pm\delta}$ as a catalyst for thermochemical hydrogen production. The first temperature and the second temperature of the thermal cycle were 1,400° C. and 800° C., respectively.

In the case of using $(La_{0.8}Sr_{0.2})MnO_{3\pm\delta}$ as the catalyst for thermochemical hydrogen production, the hydrogen production amount gradually increased with the cycle and became constant at approximately the fourth cycle.

In the case of using $(La_{0.8}Sr_{0.2})(Mn_{0.85}Ti_{0.15})O_{3\pm\delta}$ as the catalyst for thermochemical hydrogen production, the hydrogen production amount gradually decreased with the cycle.

In the case of using $(La_{0.8}Sr_{0.2})(Mn_{0.85}Fe_{0.15})O_{3\pm\delta}$ as the catalyst for thermochemical hydrogen production, the hydrogen production amount gradually decreased with the cycle.

In the case of using $(La_{0.8}Sr_{0.2})(Mn_{0.85}Ni_{0.15})O_{3\pm\delta}$ as the catalyst for thermochemical hydrogen production, the hydrogen production amount gradually decreased with the cycle. At the ninth cycle, the hydrogen production amount became substantially the same as the case of using $(La_{0.8}Sr_{0.2})MnO_{3\pm\delta}$.

In the case of using $(La_{0.8}Sr_{0.2})(Mn_{0.85}Mg_{0.15})O_{3\pm\delta}$ as the catalyst for thermochemical hydrogen production, the hydrogen production amount gradually decreased with the cycle.

In the case of using $(La_{0.8}Sr_{0.2})(Mn_{0.85}Ti_{0.15})O_{3\pm\delta}$, and $(La_{0.8}Sr_{0.2})(Mn_{0.85}Mg_{0.15})O_{3\pm\delta}$, the hydrogen production amount was approximately 3 ml/g.

In the case of using $(La_{0.8}Sr_{0.2})MnO_{3\pm\delta}$, $(La_{0.8}Sr_{0.2})(Mn_{0.85}Fe_{0.15})O_{3\pm\delta}$, and $(La_{0.8}Sr_{0.2})(Mn_{0.85}Ni_{0.15})O_{3\pm\delta}$, the hydrogen production amounts at the first cycle were approximately 5 ml/g, 6 ml/g, and 7 ml/g, respectively, but approaching the tenth cycle, all of the hydrogen production amounts became approximately 6 ml/g.

Figure 9:
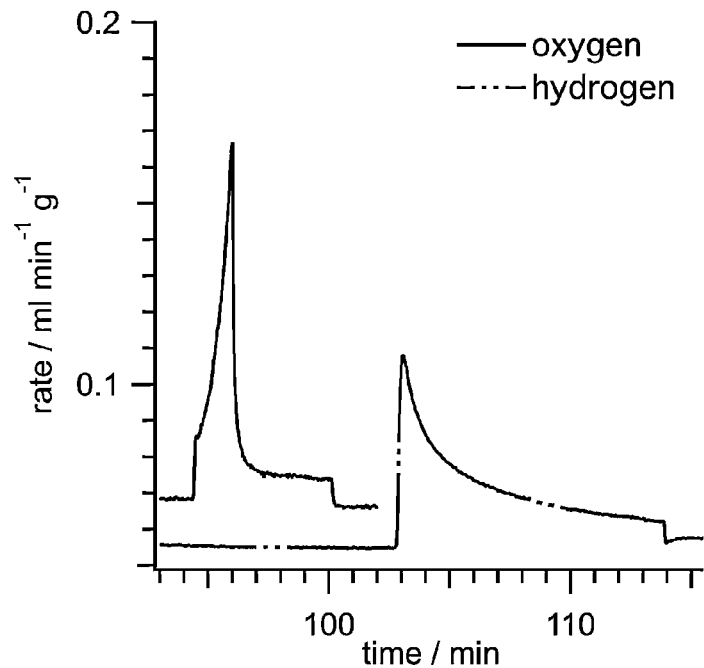
FIG. 9 is a graph illustrating a hydrogen production amount and an oxygen production amount in a case where $(La_{0.8}Sr_{0.2})CrO_{3\pm\delta}$ as a catalyst for producing thermochemical hydrogen is used, a first temperature is set to 1,300° C., and a second temperature is set to 800° C.

FIG. 9 shows a graph illustrating a hydrogen production amount and an oxygen production amount in a case of using $(La_{0.8}Sr_{0.2})CrO_{3\pm\delta}$ as the catalyst for thermochemical hydrogen production. The production amount is indicated by a flow rate (ml/min/g) per unit gram. The first temperature and the second temperature of the thermal (thermochemical) cycle were 1,400° C. and 800° C., respectively.

Figure 10:
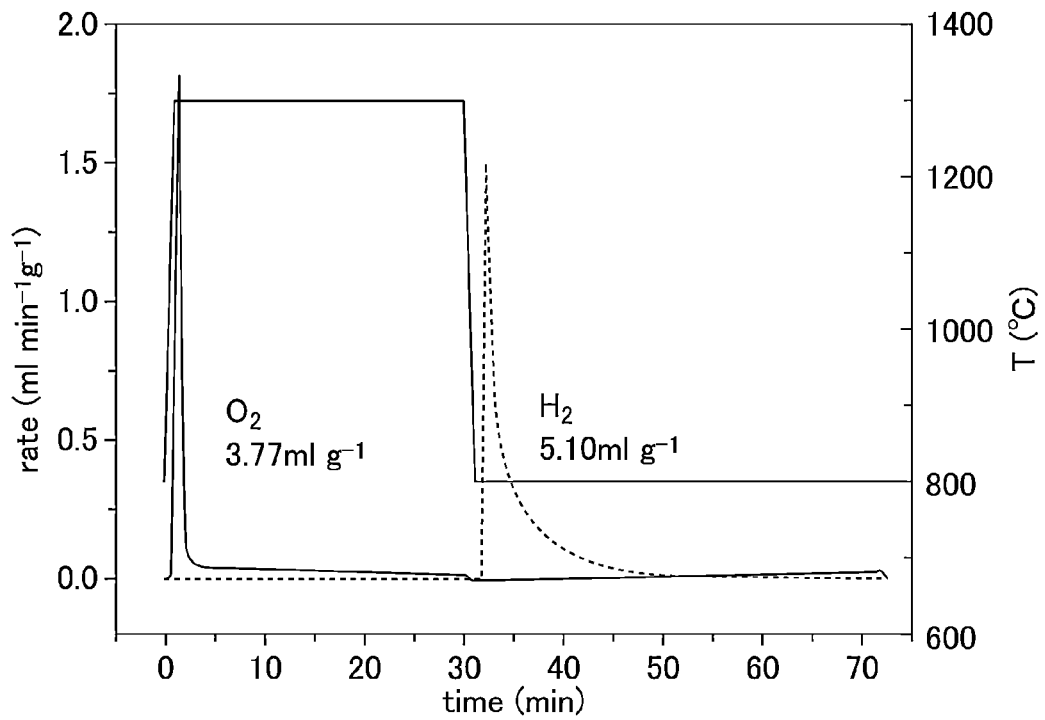
FIG. 10 is a graph illustrating a hydrogen production amount and an oxygen production amount in a case where $(La_{0.8}Sr_{0.2})CrO_{3\pm\delta}$ as a catalyst for producing thermochemical hydrogen is used, a first temperature is set to 1,500° C., and a second temperature is set to 800° C.

FIG. 10 shows a graph illustrating a hydrogen production amount and an oxygen production amount in the case of using $(La_{0.8}Sr_{0.2})CrO_{3\pm\delta}$ as the catalyst for producing thermochemical hydrogen similarly to FIG. 9. The first temperature and the second temperature of the thermal (thermochemical) cycle were 1,500° C. and 800° C., respectively.

When the first temperature was set to 1,500° C., the flow rates and the production amounts of hydrogen and oxygen were improved, respectively.

Figure 11:
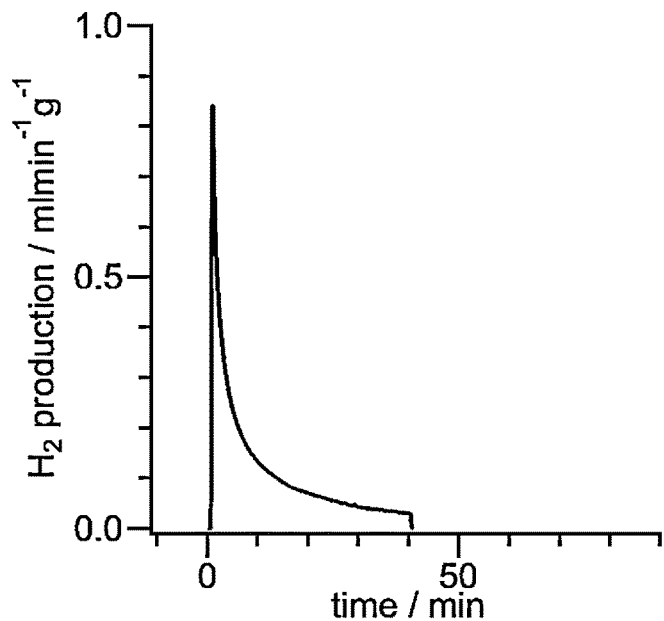
FIG. 11 is a graph illustrating a hydrogen production amount in the case of using $Ba(Ti_{0.6}Mn_{0.4})O_{3\pm\delta}$ as a catalyst for thermochemical hydrogen production.

FIG. 11 shows a graph illustrating the hydrogen production amount in the case of using $Ba(Ti_{0.6}Mn_{0.4})O_{3\pm\delta}$ as the catalyst for thermochemical hydrogen production. The first temperature and the second temperature of the thermal (thermochemical) cycle were 1,400° C. and 800° C., respectively.

As shown in FIG. 11, even when perovskite oxide in which an A site is allocated to Ba, and an X site is allocated to Mn and Ti is used in the catalyst for producing thermochemical hydrogen, hydrogen may be produced in a thermochemical manner.

Figure 12:
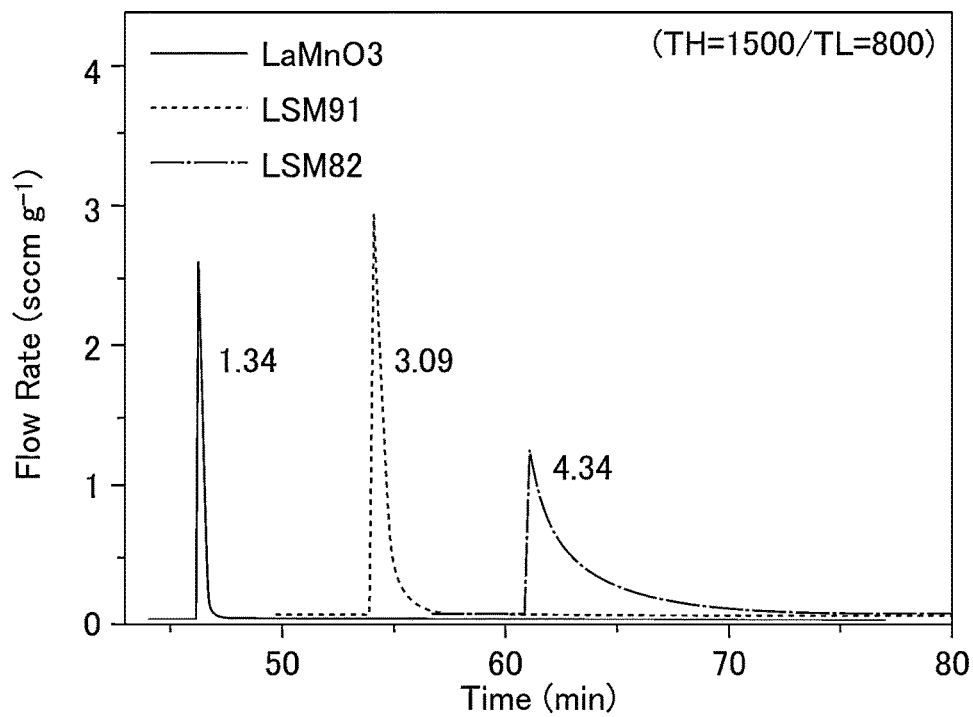
FIG. 12 is a graph illustrating a cycle characteristic of a hydrogen production amount in the case of using $La_{1-x}Sr_xMnO_{3\pm\delta}$ (x=0, 0.1, 0.2) as a catalyst for thermochemical hydrogen production.

FIG. 12 shows a graph illustrating a cycle characteristic of the hydrogen production amount in the case of using $La_{1-x}Sr_xMnO_{3\pm\delta}$ (x=0, 0.1, 0.2) as the catalyst for producing thermochemical hydrogen. The production amount is indicated by a flow rate (sccm/g) per unit gram. The first temperature and the second temperature of the thermal (thermochemical) cycle were 1,500° C. and 800° C., respectively.

The higher the concentration of Sr was, the further the hydrogen production amount increased, and the hydrogen production amount in the case of x=0.2 was 3 times that in the case of x=0.

Figure 13:
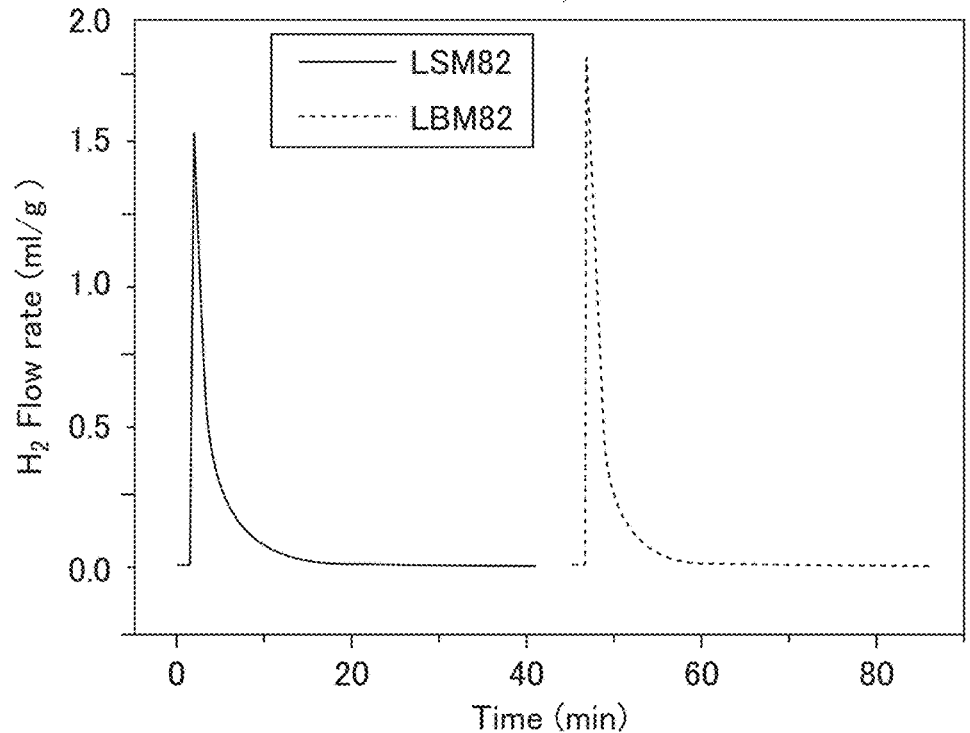
FIG. 13 is a graph illustrating a hydrogen production amount in the case of using $(La_{0.8}Sr_{0.2})MnO_{3\pm\delta}$ and $(La_{0.8}Ba_{0.2})MnO_{3\pm\delta}$ as a catalyst for thermochemical hydrogen production.

FIG. 13 shows a graph illustrating a hydrogen production amount in the case of using $(La_{0.8}Sr_{0.2})MnO_{3\pm\delta}$ and $(La_{0.8}Ba_{0.2})MnO_{3\pm\delta}$ as a catalyst for thermochemical hydrogen production. The production amount is indicated by a flow rate (ml/min/g) per unit gram. The first temperature and the second temperature of the thermal (thermochemical) cycle were 1,400° C. and 800° C., respectively.

Even when the perovskite oxide in which Sr of $(La_{0.8}Sr_{0.2})MnO_{3\pm\delta}$ was substituted with Ba was used in the catalyst for thermochemical hydrogen production, the hydrogen production amount was not changed too much.

Figure 14:
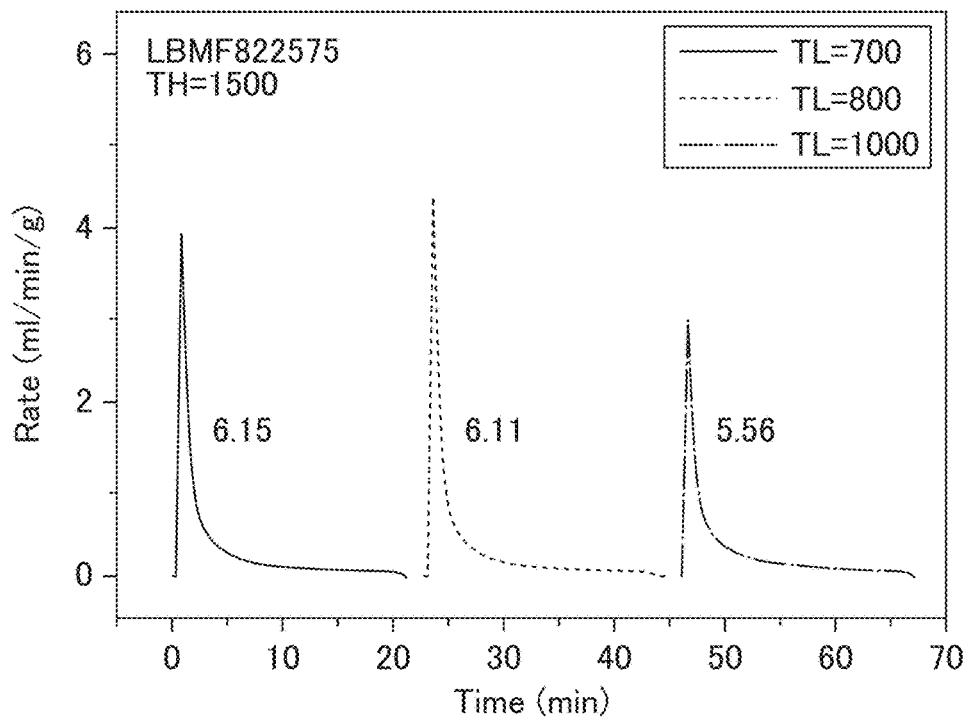
FIG. 14 is a graph illustrating a hydrogen production amount in the case of using $(La_{0.8}Ba_{0.2})(Mn_{0.25}Fe_{0.75})O_{3\pm\delta}$ as a catalyst for thermochemical hydrogen production.

FIG. 14 is a graph illustrating the hydrogen production amount in the case of using $(La_{0.8}Ba_{0.2})(Mn_{0.25}Fe_{0.75})O_{3\pm\delta}$ as the catalyst for thermochemical hydrogen production. The production amount is indicated by a flow rate (ml/min/g) per unit gram. The first temperature of the thermal (thermochemical) cycle was 1,400° C., but the second temperatures thereof were 700° C., 800° C., and 1,000° C., respectively.

In the case where the second temperatures were 700° C. and 800° C., the hydrogen production amount did not vary largely. However, conversely, in the case where the second temperature was 1,000° C., the hydrogen production amount decreased compared to the case in which the second temperatures were 700° C. and 800° C. by approximately 10%.

In the solar thermochemical hydrogen production, the concentrated solar energy needs to be absorbed by the perovskite oxide. The solar spectrum ranges from ultraviolet to visible and infrared region (250 nm to over 2700 nm). The absorbed photon excites electrons from the lower-state to the excited state, which will eventually be converted to heat via phonon. The solar absorbance measurement shows that the $La_{0.8}Sr_{0.2}Mn_{0.25}Fe_{0.75}O_{3\pm\delta}$ perovskite absorbs solar energy quite efficiently, at 4 times of ceria.

The elements composed in the perovskite are quite earth abundant. The earth abundance of iron and manganese are 35 and 0.6 times the earth abundance of carbon, respectively. Strontium (Sr) exists in the earth crust 5 times more than copper (Cu), and the lanthanum (La) is a half of copper.

In summary, the present inventors developed catalytic $La_{0.8}Sr_{0.2}Mn_{1-x}Fe_xO_{3\pm\delta}$ perovskites for thermochemical hydrogen production by mimicking the catalytic center of $Mn_4CaO_5$ cluster in photosystem II. Particularly, $La_{0.8}Sr_{0.2}Mn_{0.25}Fe_{0.75}O_{3\pm\delta}$ produces 5.3 ml/g of hydrogen in the thermochemical cycle between 800 and 1400° C. The advantages of utilizing nonstoichiometric perovskite over undoped ceria are more efficient solar absorbance by 4 times or less, the earth abundant element utilization for scalable solar fuel production, and lower temperature operation at 1200 to 1400° C. The strontium which is abundant in the Earth in this system is completely soluble in lanthanum, and it is possible to mimic the rare-earth utilization in the catalytic perovskite.

The invention will allow the conversion of solar energy into chemical fuel in high efficiency and the storage thereof, and the obtained chemical fuel will be used as clean energy in the field of each industry and as clean industrial raw materials in chemical industry.

The invention claimed is:

1. A method of producing fuel, the method comprising:
   a process of heating a perovskite oxide having a compositional formula of $AXO_{3\pm\delta}$ (provided that, $0\leq\delta<1$) to a first temperature to reduce the perovskite oxide; and
   a process of bringing carbon dioxide and/or water vapor that is a raw material gas into contact with the reduced perovskite oxide and oxidizing the perovskite oxide to produce the fuel, at a second temperature,
   wherein the method produces the fuel from thermal energy by providing a two-step thermochemical cycle of the first temperature and the second temperature, wherein the second temperature is equal to or lower than the first temperature,
   in the perovskite oxide the element A is La, the element X is Mn, wherein La is partially substituted with Sr, and Mn is partially substituted with Fe; and
   each atom of Mn is partially substituted with 0.35 to 0.85 atoms of Fe.

2. The method of producing fuel using thermochemical fuel production according to claim 1,
   wherein the fuel is any one of hydrogen, methane, and methanol.

3. The method of producing fuel using thermochemical fuel production according to claim 1,
   wherein the raw material gas includes water vapor.

4. The method of producing fuel using thermochemical fuel production according to claim 1,
   wherein the raw material gas includes carbon dioxide and water vapor.

\* \* \* \* \*